United States Patent [19]

Ahrens et al.

[11] Patent Number: 5,641,111
[45] Date of Patent: Jun. 24, 1997

[54] SURGICAL STAPLING INSTRUMENT WITH ANVIL CUTTING GUIDE

[75] Inventors: Brenton K. Ahrens, West Chester; James N. Wisner; Daniel Huston, both of Cincinnati; Ronald Adams, Wyoming; Daniel Price, Loveland; Benjamin Gaw, Cincinnati, all of Ohio

[73] Assignee: Ethicon Endo-Surgery, Inc., Cincinnati, Ohio

[21] Appl. No.: 496,232

[22] Filed: Jun. 28, 1995

[51] Int. Cl.$^6$ .................................................. A61B 17/068
[52] U.S. Cl. ........................ 227/175.1; 227/19; 227/180.1
[58] Field of Search ................................ 227/19, 175.1, 227/176.1, 179.1, 180.1

[56] References Cited

U.S. PATENT DOCUMENTS

| | | | |
|---|---|---|---|
| 4,485,811 | 12/1984 | Chernousou et al. | 227/19 |
| 4,715,520 | 12/1987 | Roehr, Jr. et al. | 227/19 |
| 5,100,042 | 3/1992 | Gravener et al. | 227/19 |
| 5,137,198 | 8/1992 | Nobis et al. | 227/19 |

*Primary Examiner*—Scott A. Smith
*Attorney, Agent, or Firm*—Matthew S. Goodwin

[57] ABSTRACT

An anvil for a surgical fastener assembly is disclosed. The anvil has a staple-forming surface upon which a plurality of pockets are displayed for staple formation. First and second sidewalls extend from the staple-forming surface. Cutting guides extend laterally from the sidewalls to provide a uniform surface upon which a user can apply pressure with a scalpel to staple tissue in a direction generally parallel to the vertical staple row. An even margin can be maintained between the staple row and the cut line, thus increasing the degree of confidence and skill that the user can employ when cutting the fastened tissue.

9 Claims, 4 Drawing Sheets

SURGICAL STAPLING INSTRUMENT WITH ANVIL CUTTING GUIDE

BACKGROUND OF THE INVENTION

This invention relates generally to surgical instruments for fastening bodily tissue. More specifically, it relates to instruments carrying an anvil upon which staples are formed to fasten the tissue.

Surgical staplers include a fastener assembly carrying an anvil upon which staples are fired. Linear staplers fire vertical rows of staples to fasten tissue. The fastener assembly includes not only the anvil but also a cartridge carrying the staples to be fired. Tissue is first clamped between the cartridge and anvil, and then the staples are fired from the cartridge, through the tissue and against the anvil where the staples are formed. Linear staplers come in different sizes, depending on the desired length of vertical rows of the staples which need to be placed to fasten the tissue. The cartridge has an elongated housing, and vertical rows of slots in the housing to receive the staples. Correspondingly, the anvil has an elongated body, and vertical rows of pockets on its tissue contacting surface. Each pocket is in alignment with a corresponding slot in the housing of the cartridge. When tissue is clamped between the elongated cartridge and housing, the staples are fired from the slots against the pockets on the anvil.

After a linear stapler is fired, it is frequently necessary to cut the fastened tissue on one side of the staple row with a scalpel. However, in order to cut, a surface must exist which allows the user to exert pressure against the surface while concurrently cutting tissue in a direction generally parallel to the staple row which has been fired into tissue. Frequently, the jaw providing the main frame subassembly for the fastener assembly, often referred to as the "hook", provides the cutting surface. This is so because the hook has a channel into which the anvil is placed. In other words, the anvil is sandwiched between the sidewalls of the channel. The tissue contacting surface of the anvil which contains the pockets against which the staples are formed extends beyond the channel, and the edge surfaces on the sidewalls of the channel can then provide the cutting surface for the scalpel when tissue needs to be cut after the staples are fired.

Unfortunately, the edge surfaces of the sidewalls of the channels on the "hook" do not provide a well-defined edge against which a scalpel can be placed for ease of curing stapled tissue. This edge does not provide a consistent margin between the staple line and the cut location.

Alternately, the construction of the linear stapler can be modified such that the hooks are sandwiched between the anvil. The tissue contacting surface of the anvil which contains the pockets against which the staples are formed extends beyond the hooks. Therefore, the edge surfaces forming the cutting guide on the sidewalls of the channel are covered by the anvil. In this configuration, the hook and anvil assembly are narrower. This narrower assembly permits better and easier access to the tissue which is to be stapled. Unfortunately, while better access with this particular configuration may be obtained, there is no cutting guide present in the instrument.

In view of the deficiencies inherent with surgical fastener assemblies of surgical staplers, what is needed is an anvil for the surgical fastener assembly which incorporates the feature of a uniform cutting guide to cut the stapled tissue. What is needed is a guide which will not change its relative location or size, unlike the conventional use of the edge of the sidewalls of the hooks in which the anvil is routinely placed. Ideally, this guide can be used with a narrow hook and anvil assembly. Furthermore, what is needed is a cutting guide for an anvil which provides a well-defined edge or surface against which a scalpel can be placed for ease of cutting stapled tissue. Finally, a cutting guide which can provide a consistent margin between the staple row and the cut location would be highly desirable.

SUMMARY OF THE INVENTION

The invention is an anvil for a surgical fastener assembly. The anvil comprises an elongated body having first and second ends. The body has a staple-forming surface on it extending generally from the first to the second ends. This surface displays a plurality of pockets in the surface. The body of the anvil has mutually opposed first and second sidewalls extending from the staple forming surface from the first to the second ends. Significantly, first and second curing guides extend laterally from the first and second sidewalls, respectively.

The incorporation of the cutting guides onto the sidewalls of the elongated body of the anvil specifically addresses the problems inherent in conventional surgical staplers containing surgical fastener assemblies. Specifically, the cutting guide provides a uniform surface against which the user can apply pressure with a scalpel to cut stapled tissue in a direction generally parallel to the staple row. The cutting guide provides a consistent margin between the staple row and the cut line. Since the guide is incorporated onto the anvil, its relative location and size will not vary. Therefore, the user can cut the tissue consistently and confidently.

In addition, incorporation of the cutting guide onto the sidewalls of the anvil permits the hooks to be sandwiched between the anvil, which decreases the overall size of this portion of the instrument. Decreasing the size of the anvil and hooks affords better access to the tissue which is to be stapled without compromising the function of the instrument.

The anvil of this invention can be used in any surgical fastener assembly of a surgical stapler. It can be incorporated into a stapler to be used for conventional, open surgical procedures, or endoscopic surgical procedures.

DETAILED DESCRIPTION OF THE PREFERRED EMBODIMENT

Figure 1:
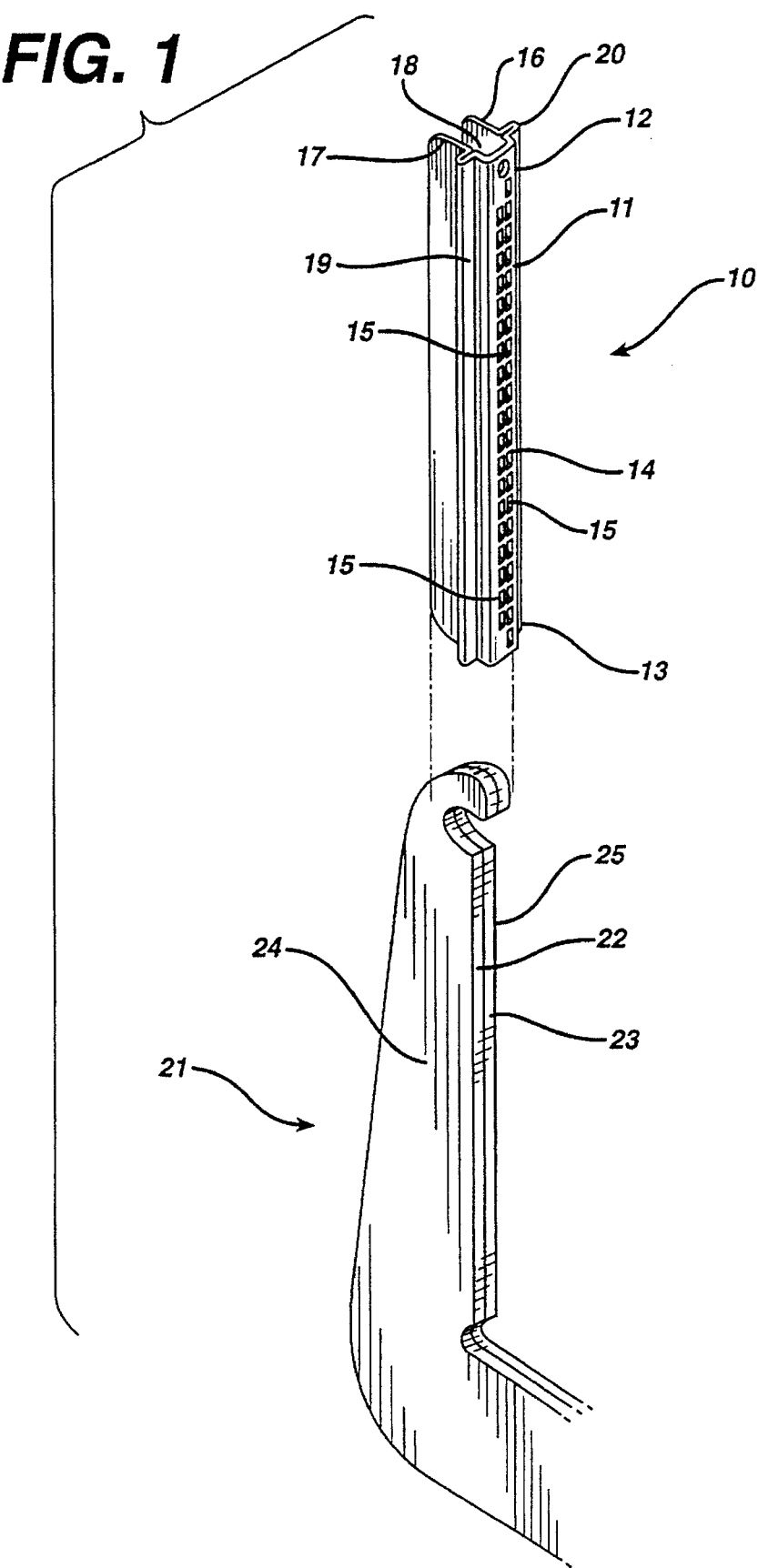
FIG. 1 is an exploded perspective view of the anvil of this invention and how it is positioned on the hook of a surgical fastener assembly for a linear stapler.

The preferred anvil of this invention is depicted clearly in FIG. 1. The anvil 10 has an elongated, solid body 11. The anvil is preferably composed of a metal, such as stainless steel, although other materials such as plastics can be used. The elongated body has first and second ends 12 and 13, respectively. A generally planar, staple-forming surface 14 extends from the first through the second ends. The width of the staple forming surface is sufficient to provide for a plurality of staple-forming pockets 15 imbedded into the surface. In the embodiment depicted in FIG. 1, two adjacent vertical rows of pockets imbedded on the staple forming surface extend from the first to the second end of the elongated body of the anvil.

The anvil has first and second sidewalls 16 and 17, respectively, extending from the staple forming surface of the elongated body. The sidewalls extend from the first to the second end of the elongated body, and mutually oppose each other. Each of the sidewalls are rectangular in shape, and are displayed perpendicularly relative to the staple forming surface. The width of each sidewall and the distance between them is such that a channel 18 is formed on the underside of the staple-forming surface which extends from the first to the second end of the elongated body. Preferably, the width of the channel is the same as the width of the staple forming surface.

A precise cutting surface is provided on the body of the anvil with first and second cutting guides 19 and 20, respectively. The cutting guides extend laterally from each sidewall from the first to the second end of the elongated body. The cutting guides are generally perpendicular to the sidewalls and parallel to the staple forming surface. The cutting guides are preferably substantially identical to each other, and each guide can be described as an elongated ridge protruding outwardly from the sidewall surface. Each of the ridges preferably has a constant lateral dimension relative to the sidewall surface. In a preferred embodiment, the first and second cutting guides have chamfered ends (not shown). By chamfering the ends of the cutting guides, the cutting guides will be atraumatic when presented to the tissue.

The anvil of this invention can conveniently be made from a single piece of sheet metal using conventional manufacturing techniques. The ridges which form the cutting guides can be formed from the sidewall surfaces by "sandwiching" adjacent portions of the sidewall surfaces together to form the ridge. The pockets can be formed on the staple forming surface using conventional coining or stamping techniques. Alternatively, the anvil can be made from a plastic using conventional injection molding methods.

The channel formed between the first and second sidewalls of the anvil can be fitted over the hook of a surgical fastener assembly of a linear stapler. As illustrated in FIG. 1, the surgical fastener assembly of a linear stapler typically includes a structural hook 21 having first and second hook elements 22 and 23, respectively. In this embodiment, the hook elements are mated to each other in tandem contact. The first and second hook elements have first and second sidewall contacting surfaces 24 and 25, respectively. The anvil of this invention is secured to the hook when the hook elements are situated within the anvil channel, and the internal surfaces of sidewalls of the anvil are in press-fit contact with the sidewall contacting surfaces of the hook elements.

Figure 2:
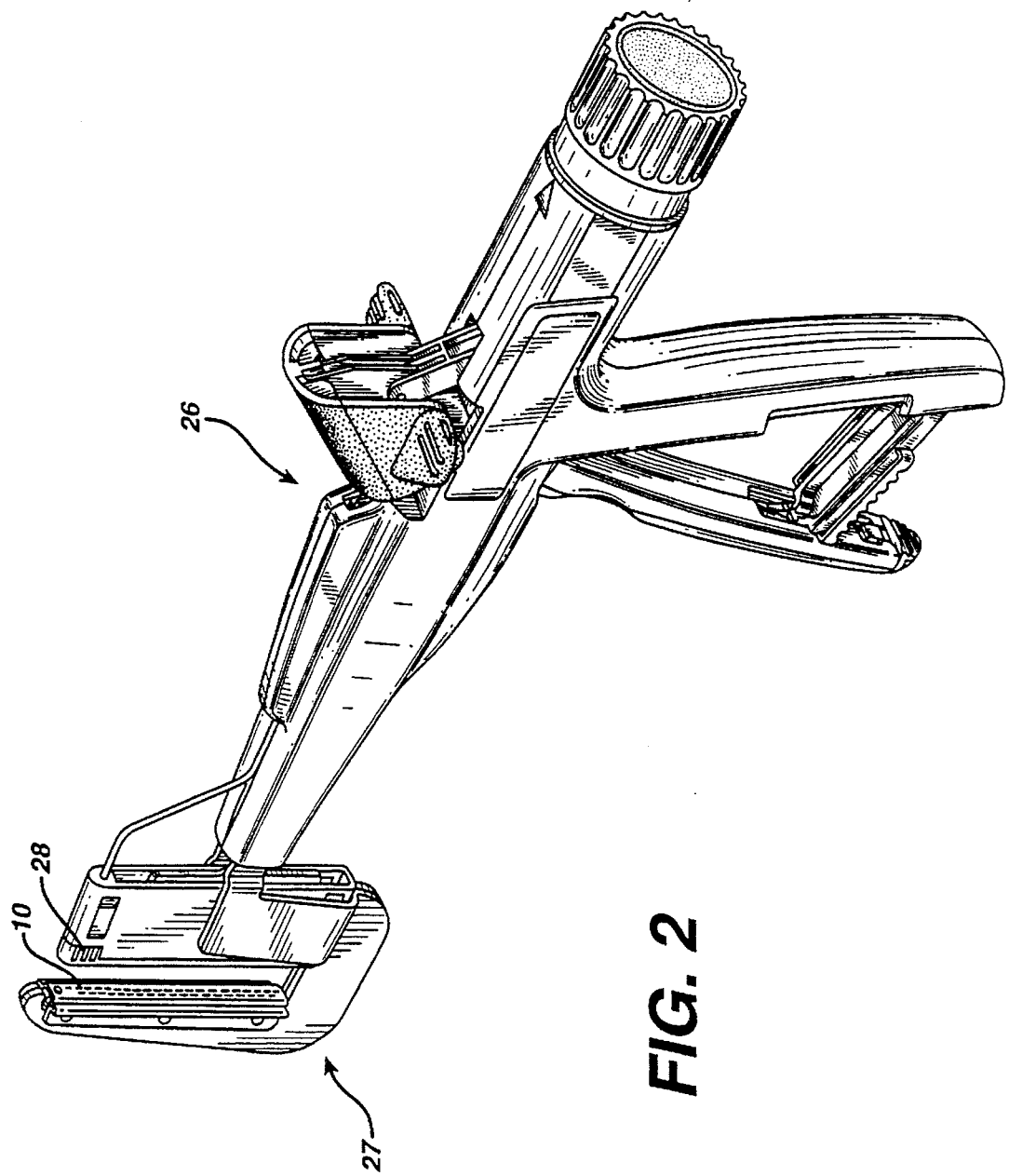
FIG. 2 is a perspective view of a linear stapler with a surgical fastener assembly which has the anvil of this invention.

Referring now to FIG. 2, there is illustrated a conventional linear stapler 26 which has a surgical fastener assembly 27 including the anvil 10 of this invention. The details of this linear stapler are described in U.S. Pat. No. 5,137, 198. The surgical fastener assembly of the stapler includes a cartridge assembly 28. When it is desired to fasten tissue, tissue is placed in the tissue fastener assembly between the anvil and the cartridge assembly. When the tissue is positioned, the cartridge assembly is moved forwardly to clamp the tissue. Staples can then be fired into the clamped tissue from the cartridge assembly for formation against the staple forming surface of the anvil. When the staples have been fired, it is often desirable to subsequently cut the tissue adjacent the row of staples which have been fired.

Figure 3:
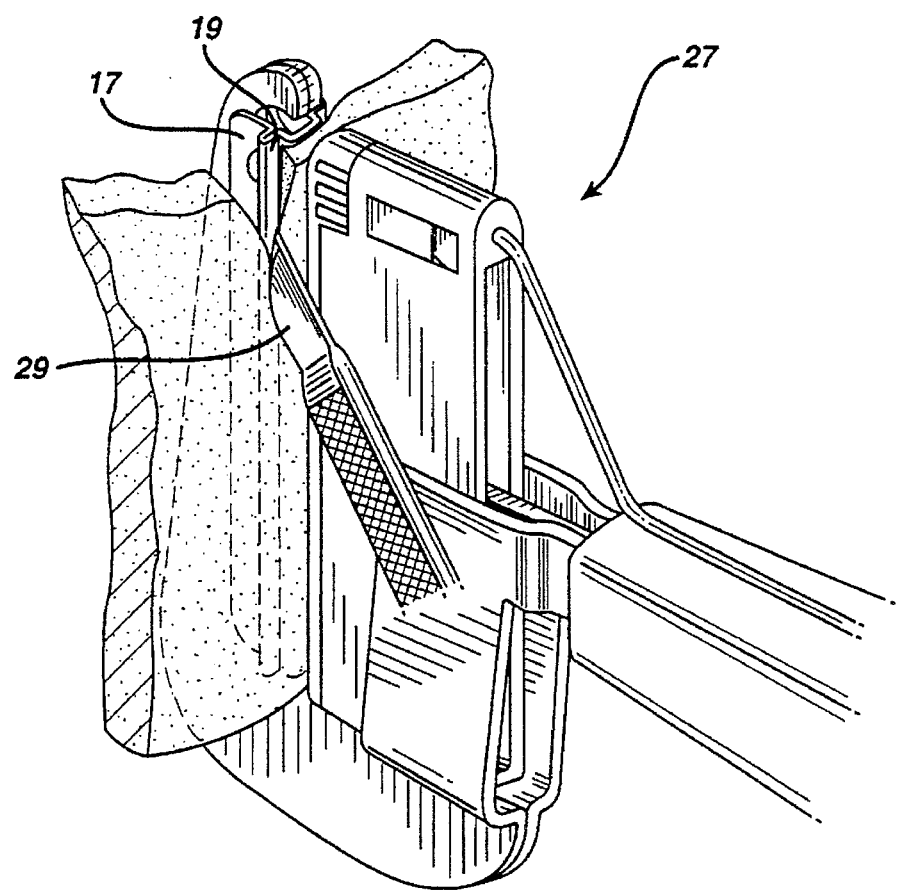
FIG. 3 is a large partial perspective view showing tissue clamped in a surgical fastener assembly of the linear stapler illustrated in FIG. 2, and how the cutting guide on the anvil of this invention provides a surface for cutting the clamped tissue.
Figure 4:
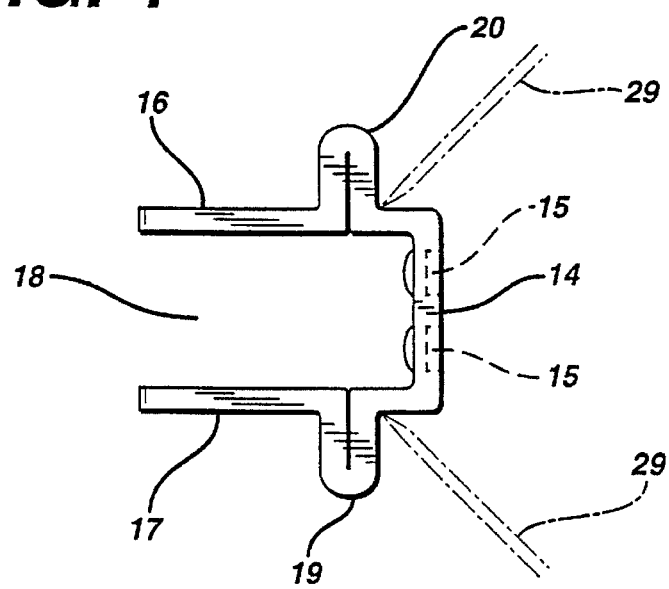
FIG. 4 is a top plan view of the anvil of this invention.

FIG. 3 illustrates the convenient surface which the integral cutting guide 19 extending laterally from the sidewall 17 of the anvil provides two cut the fastened tissue. A scalpel 29 can be used to cut the tissue at the junction between the sidewall the cutting guide. A constant, continuous surface is therefore provided to cut the tissue. Consequently, the cut line will be relatively straight and create a constant margin between the stapled tissue and the cut line. The optimal positioning of the scalpel once the tissue is cut is depicted in FIG. 4.

Figure 5:
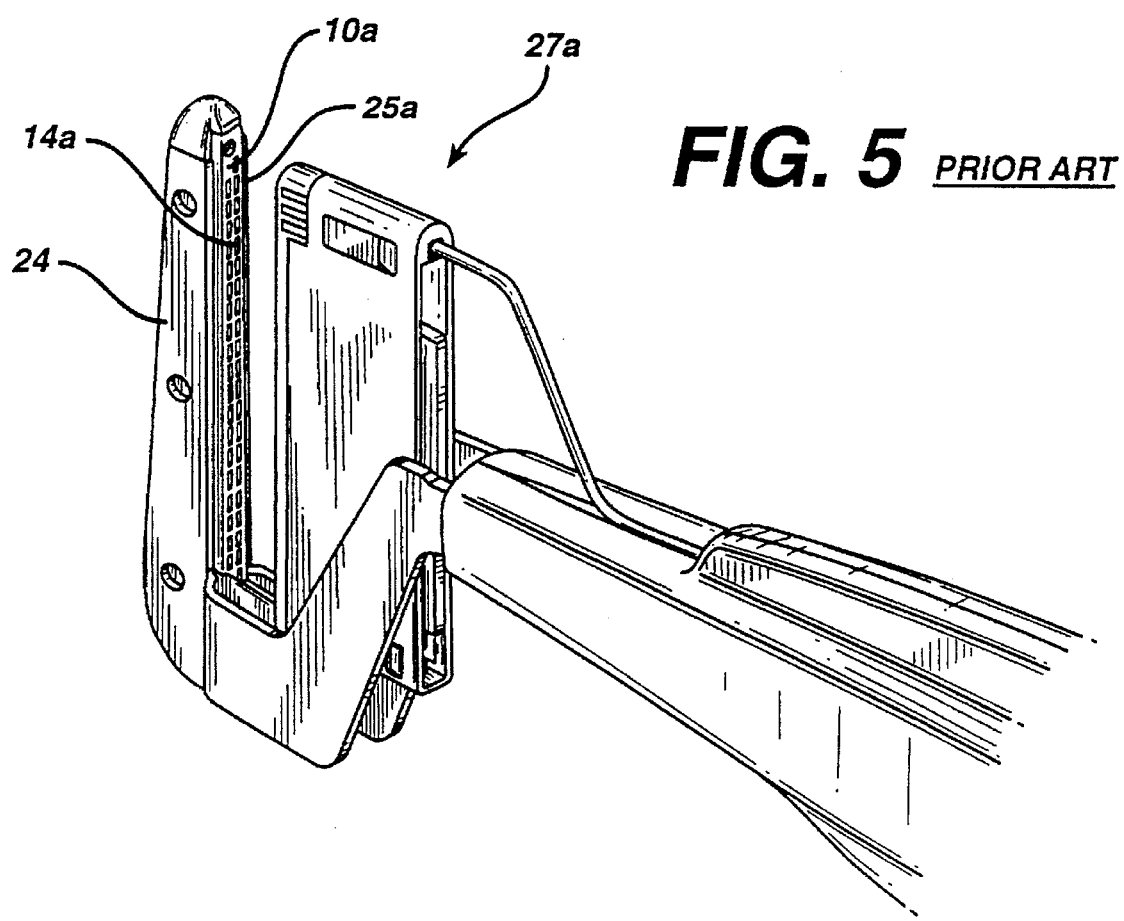
FIG. 5 is a perspective view of a surgical fastener assembly incorporating the prior art anvil.

Referring to FIG. 5, there is shown a surgical fastener assembly 27a of a linear stapler which includes the prior art anvil 10a. Unlike the anvil of this invention, the prior art anvil does not have cutting guides extending laterally from the sidewalls of the anvil to facilitate the cutting of the tissue. The first and second hook elements 24a and 25a are spaced apart from each other to provide a channel between them for receiving the anvil. The staple-forming surface 14a of the anvil protrudes from the hook elements. Therefore, the only surface which can be used to cut tissue after staples have been fired into the tissue is the edge surface of each hook element situated adjacent the sidewalls of the anvil.

Although this invention has been described in connection with its most preferred embodiment, this description should not be used to impute limitations into the claimed invention which have not been expressly set forth in the claims which appear below. This description is illustrative only, and numerous additional embodiments will become apparent to those skilled in this art. For example, although the anvil of this invention has been described in connection with a convention linear stapler, it can be used with other staplers, including endoscopic staplers. In addition, although the preferred anvil is described as a one-piece anvil, it can be manufactured from more than one piece. For example, the first and second cutting guides can be made separately from the remainder of the anvil, and the first and second cutting guides can be snap-fit onto the sidewalls of the anvil.

What is claimed is:

1. An anvil for a surgical fastener assembly wherein said assembly includes a structural hook for supporting said anvil, said anvil comprising an elongated body having first and second ends, a staple-forming surface thereon extending generally from said first to said second ends, said surface displaying a plurality of pockets therein, mutually opposed first and second sidewalls extending from said staple-forming surface from said first to said second ends, said first and second sidewalls forming a channel therebetween for receiving said structural hook therein, and first and second cutting guides extending laterally from said first and second sidewalls, respectively.

2. The anvil of claim 1 wherein said sidewalls are generally perpendicular to said staple-forming surface.

3. The anvil of claim 2 wherein said laterally extending cutting guides are generally perpendicular to said sidewalls and generally parallel to said staple-forming surface.

4. The anvil of claim 3 wherein said cutting guides extend from said first to said second ends of said elongated body.

5. The anvil of claim 4 wherein said cutting guides extend continuously from said first to said second ends of said elongated body.

6. The anvil of claim 5 wherein said cutting guides have a generally constant lateral dimension.

7. The anvil of claim 6 wherein said cutting guides extend integrally from said sidewalls.

8. The anvil of claim 7 wherein said sidewalls extend integrally from said staple-forming surface, and said anvil is a one-piece anvil.

9. The anvil of claim 8 wherein said pockets are arranged in at least two vertical rows.

* * * * *